United States Patent
Brand et al.

(10) Patent No.: US 7,528,254 B2
(45) Date of Patent: May 5, 2009

(54) PROCESS FOR PREPARING MONTELUKAST AND SALTS THEREOF

(75) Inventors: Michael Brand, RaAnana (IL); Moty Shookrun, Petach-Tikva (IL); Oded Arad, Rechovot (IL); Joseph Kaspi, Givatayim (IL)

(73) Assignee: Chemagis Ltd., Bnei-Brak (IL)

( * ) Notice: Subject to any disclaimer, the term of this patent is extended or adjusted under 35 U.S.C. 154(b) by 0 days.

(21) Appl. No.: 11/711,042

(22) Filed: Feb. 27, 2007

(65) Prior Publication Data

US 2007/0208178 A1    Sep. 6, 2007

Related U.S. Application Data

(60) Provisional application No. 60/776,693, filed on Feb. 27, 2006.

(51) Int. Cl.
*C07D 215/14*     (2006.01)

(52) U.S. Cl. ..................................................... 546/180

(58) Field of Classification Search .................. 546/180
See application file for complete search history.

(56) References Cited

U.S. PATENT DOCUMENTS

| 5,523,477 A | 6/1996 | King et al. |
| 5,614,632 A | 3/1997 | Bhupathy et al. |

FOREIGN PATENT DOCUMENTS

| EP | 480717 | 10/1991 |
| WO | WO 2005/105751 | 11/2005 |
| WO | 2006/058545 A1 * | 6/2006 |
| WO | 2006/064269 A2 * | 6/2006 |

* cited by examiner

*Primary Examiner*—Taofiq A Solola

(57) ABSTRACT

The present invention provides a process for preparing highly pure montelukast and salts thereof by reacting the side-chain precursor 1-(mercaptomethyl)-cyclopropaneacetic acid with 2-(2-(3S)-(3-(7-chloro-2-quinolinyl)-ethenyl)phenyl)-3-(methanesulfonyloxypropyl)phenyl-2-propanol in a solvent mixture containing a base.

29 Claims, No Drawings

PROCESS FOR PREPARING MONTELUKAST AND SALTS THEREOF

RELATED APPLICATIONS

The present application claims priority from U.S. Provisional Patent Application No. 60/776,693, filed on Feb. 27, 2006, which is incorporated herein by reference in its entirety.

FIELD OF THE INVENTION

The field of the invention relates to an improved process for preparing montelukast and salts thereof.

BACKGROUND OF THE INVENTION (R-(E))-1-(((1-(3-(2-(7-chloro-2-quinolinyl)ethenyl)phenyl)-3-(2-(1-hydroxy-1-methylethyl)phenyl)propyl)thio)methyl)cyclopropaneacetic acid sodium salt, also known by the name montelukast sodium, is represented by the structural formula I below:

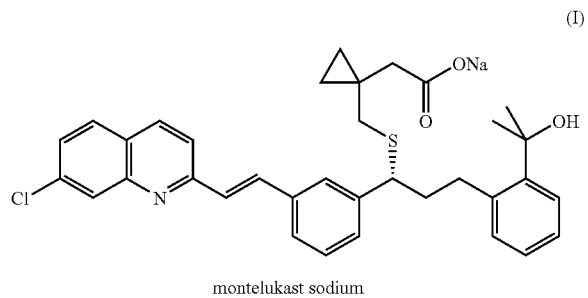

montelukast sodium

Montelukast sodium is a leukotriene antagonist, and is thus useful as an anti-asthmatic, anti-allergic, anti-inflammatory and cytoprotective agent. Montelukast sodium is currently indicated for the treatment of asthma and allergic rhinitis.

Montelukast sodium, formulated as tablets (containing 10.4 mg montelukast sodium), chewable tablets (containing 4.2 or 5.2 mg montelukast sodium) or oral granules (in a packet containing 4.2 mg montelukast sodium), is typically given once daily to the patients for the treatment of asthma and seasonal allergic rhinitis. Montelukast sodium is marketed in the United States and other countries by Merck & Co., Inc. under the trade name Singulair®.

Montelukast sodium and related compounds were first disclosed in European Patent No. EP 480,717. The synthesis of montelukast sodium, as taught in patent EP 480,717, involves coupling methyl 1-(mercaptomethyl)cyclopropaneacetate (IIa) with 2-(2-(3(S)-(3-(7-chloro-2-quinolinyl)ethenyl)phenyl)-(methanesulfonyloxypropyl) phenyl-2-propanol (III) followed by hydrolysis of the resulting montelukast methyl ester so as to form a free acid, which is followed by conversion of this montelukast free acid to a corresponding sodium salt, isolated as an amorphous material by freeze-drying.

U.S. Pat. No. 5,523,477 describes the formation of montelukast and its subsequent conversion into the dicyclohexyl ammonium salt, which is converted to montelukast sodium.

U.S. Pat. No. 5,614,632 teaches a method of preparing crystalline montelukast sodium, which involves the preparation of the dilithium dianion of 1-(mercaptomethyl)cyclopropaneacetic acid (IV), using butyl lithium, followed by condensation thereof with the mesylate alcohol (III) to yield montelukast acid as a viscous oil. The resulting montelukast acid is converted, via the corresponding dicyclohexyl ammonium salt, to crystalline montelukast sodium.

The extra purification step via the dicyclohexyl ammonium salt, which is disclosed in U.S. Pat. Nos. 5,523,477 and 5,614,632, is necessitated from the difficulties encountered in obtaining crystalline materials. Thus, the crude acid is purified via the dicyclohexylamine salt by reacting it with dicyclohexylamine in ethyl acetate, followed by addition of hexanes to effect crystallization of the dicyclohexylamine salt, or by the crystallization from toluene/heptane. It is mentioned by the inventors of patent U.S. Pat. No. 5,614,632, that the crystalline montelukast dicyclohexylamine salt offers an efficient method for the purification of montelukast, which circumvents the need to use chromatographic purification.

Another process for preparing montelukast sodium is provided in patent application WO 2005/105751 (hereinafter the '751 application). It is stated in the '751 application that butyl lithium is a dangerous and expensive material, hence there is a need for another method which avoids the use of this reagent. Thus, the '751 application provides a process for preparing montelukast sodium comprising reacting 2-(2-(3(S)-(3-(7-chloro-2-quinolinyl)ethenyl(phenyl)-3(hydroxypropyl)phenyl-2-propanol (V) with methanesulfonyl chloride to obtain 2-(2-(3(S)-(3-(7-chloro-2-quinolinyl)ethenyl)phenyl)-(methanesulfonyloxypropyl)phenyl-2-propanol (III), which is subsequently reacted with 1-(mercaptomethyl) cyclopropaneacetic acid alkyl ester (e.g., compound IIa or IIb) in a solvent and in the presence of a co-solvent and a base such as NaOH, followed by hydrolysis of the resulting product of the previous step to obtain montelukast sodium.

The synthesis of the 1-(mercaptomethyl)cyclopropaneacetic acid alkyl esters, according to the '751 application, as taught in examples 1 and 2 therein, is depicted in Scheme 1 below.

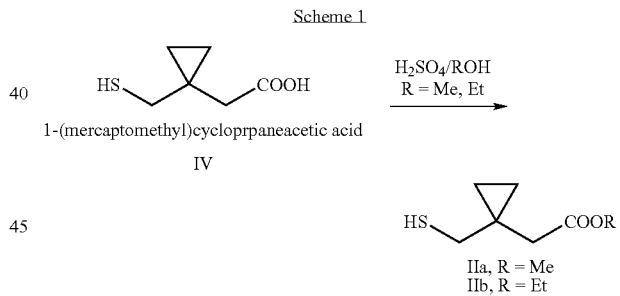

However, using one of the reagents belonging to the group of compounds 1-(mercaptomethyl)cyclopropaneacetic acid alkyl esters adds an extra synthetic step to the total synthesis of montelukast sodium, because these esters are obtained from the corresponding 1-(mercaptomethyl)cyclopropaneacetic acid.

Thus, there is still a need in the art for a method of preparing montelukast sodium, which has no additional synthetic steps in comparison to the original process described in patent U.S. Pat. No. 5,614,632 on one hand, and avoiding the use of butyl lithium on the other hand.

SUMMARY OF THE INVENTION

In one embodiment, the present invention provides a process for preparing montelukast acid and salts thereof. The process comprises reacting the compound 2-(2-(3(S)-(3-(7-chloro-2-quinolinyl)ethenyl(phenyl)-3(hydroxypropyl)phenyl-2-propanol (V) with methanesulfonyl chloride to provide the mesylate alcohol (III), which is consequently reacted with 1-(mercaptomethyl)cyclopropaneacetic acid (IV) to obtain a montelukast acid or an ammonium salt thereof e.g., the cyclohexyl, cycloheptyl or cyclooctyl ammonium salt. The isolated ammonium addition salt can be purified and converted to montelukast sodium.

Thus, the process for preparing montelukast acid and salts thereof, preferably includes:

reacting 2-(2-(3(S)-(3-(7-chloro-2-quinolinyl)ethenyl)phenyl)-3-(hydroxylpropyl)phenyl)-2 propanol (V) with methanesulfonyl chloride to obtain 2-(2-(3S)-(3-(7-chloro-2-quinolinyl)ethenyl)phenyl)-3-(methanesulfonyloxypropyl)-phenyl-2-propanol (III);

reacting compound (III) with 1-(mercaptomethyl)cyclopropaneacetic acid (IV) in a solvent mixture containing a base;

optionally isolating montelukast acid or adding an organic amine and isolating an addition ammonium salt thereof; and optionally converting the montelukast ammonium salt to montelukast sodium.

Reacting compound (V) with methanesulfonyl chloride preferably includes:

admixing compound (V) with an organic solvent;

optionally cooling to reduced temperature and adding a base;

adding methanesulfonyl chloride, optionally in several portions, and reacting for sufficient time period to allow completing the reaction;

filtering the thus formed suspension and obtaining a filtrate containing the crude product; and optionally using the filtrate in the next reaction.

Reacting compound (III) with 1-(mercaptomethyl)cyclopropaneacetic acid (IV) in a solvent mixture and in the presence of a base preferably includes:

admixing 1-(mercaptomethyl)cyclopropaneacetic acid (IV) with an organic solvent under stirring;

admixing a base and optionally a co-solvent to afford a suspension;

admixing the solution of compound (III) in an organic solvent, thus a solvent mixture containing the base is formed;

stirring for sufficient time period to allow completing the reaction; and optionally isolating montelukat acid as an oil.

In another embodiment, there is provided a process for preparing an ammonium salt of montelukast. The process comprises admixing an amine and the reaction product of compound (IV) and compound (III) to obtain an ammonium salt of montelukast, and optionally purifying the ammonium salt of montelukast. Non-limiting examples of an amine include cyclohexylamine, cyclopentylamine, cycloheptylamine, cyclooctylamine, cyclododecylamine, and phenethylamine.

In another embodiment, there is provided a process for preparing the sodium salt of montelukast from an ammonium salt, the process comprising:

admixing the ammonium salt, an acid, an organic solvent, and water;

separating the water; adding a base and water;

distilling off at least part of the organic solvent and obtaining an aqueous mixture of the final product; and drying the resulting aqueous mixture to obtain montelukast sodium.

The process disclosed herein enables obtaining Compound (I) in a total yield of about 70%. The purity is at least 98.5%, and can be more than 99%, or greater than 99.5% (as determined by HPLC).

DETAILED DESCRIPTION OF THE INVENTION

The inventors of the present invention have surprisingly discovered that it is not necessary to react 1-(mercaptomethyl)cyclopropaneacetic acid alkyl ester (e.g., compounds IIa or IIb) with the mesylate 2-(2-(3(S)-(3-(7-chloro-2-quinolinyl)ethenyl)phenyl)-3-methanesulfonyloxypropyl)phenyl-2-propanol (III), for preparing montelukast or a salt thereof and 1-(mercaptomethyl)cyclopropaneacetic acid (IV) may be used instead, without the need to use butyl lithium, and thus an extra synthetic step (of preparing the corresponding ester) can be eliminated.

In one embodiment, the present invention provides a process for preparing montelukast acid and salts thereof, which is depicted in Scheme 2 below. The process comprises reacting the compound 2-(2-(3(S)-(3-(7-chloro-2-quinolinyl)ethenyl-(phenyl)-3(hydroxypropyl)phenyl-2-propanol (V) with methanesulfonyl chloride to provide the mesylate alcohol (III), which is consequently reacted with 1-(mercaptomethyl)cyclopropaneacetic acid (IV) to obtain a montelukast acid or an ammonium salt thereof, e.g., the cyclohexyl, cycloheptyl or cyclooctyl ammonium salt. The isolated ammonium addition salt can be purified and converted to montelukast sodium.

Scheme 2

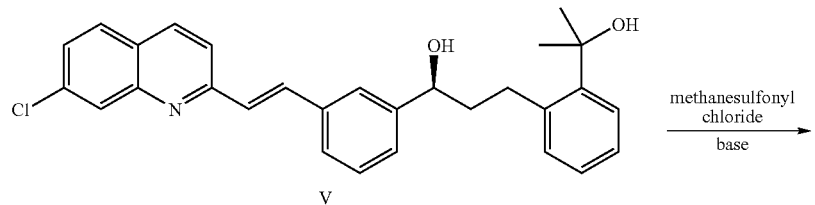

V

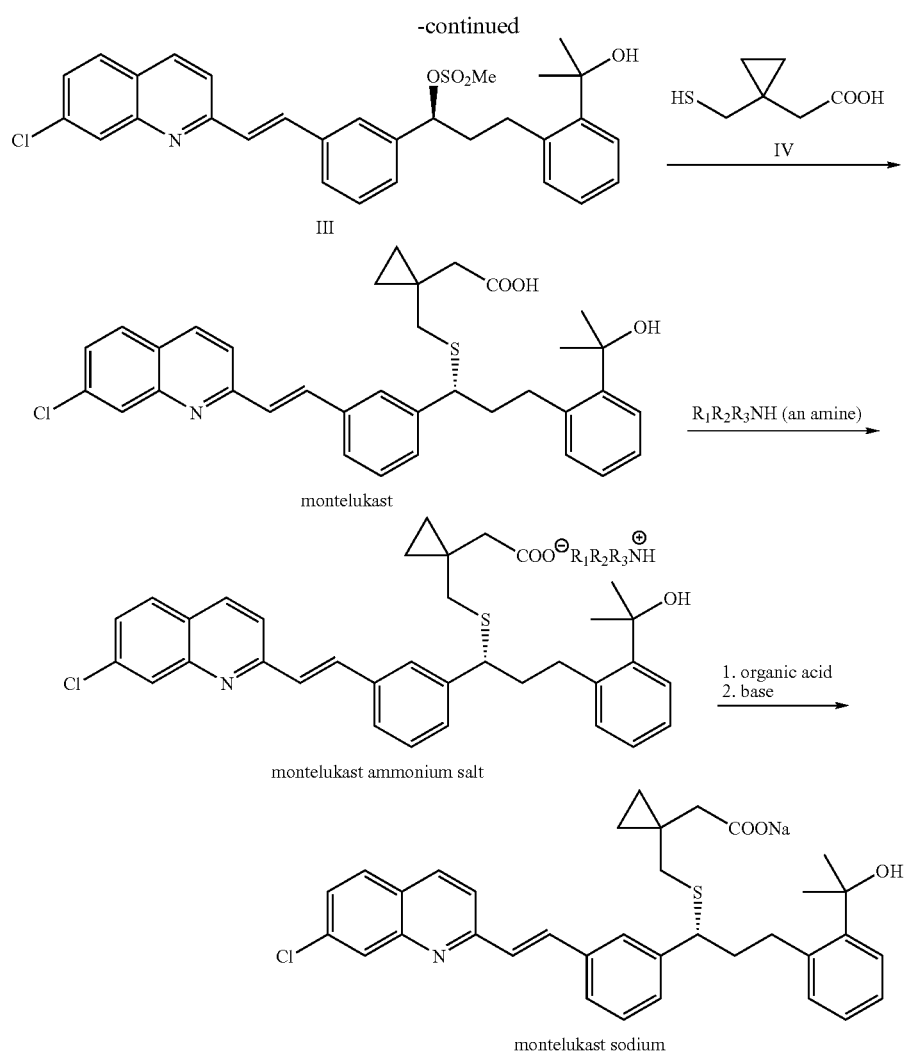

Thus, the process for preparing montelukast acid and salts thereof, preferably includes:

- reacting 2-(2-(3(S)-(3-(7-chloro-2-quinolinyl)ethenyl) phenyl)-3-(hydroxylpropyl)phenyl)-2 propanol (V) with methanesulfonyl chloride to obtain 2-(2-(3S)-(3-(7-chloro-2-quinolinyl)ethenyl)phenl)-3-(methanesulfonyloxypropyl)phenyl-2-propanol (III);
- reacting compound (III) with 1-(mercaptomethyl)cyclopropaneacetic acid (IV) in a solvent mixture containing a base;
- optionally isolating montelukast acid or adding an organic amine and isolating an addition ammonium salt thereof; and
- optionally converting the montelukast ammonium salt to montelukast sodium.

Reacting compound (V) with methanesulfonyl chloride preferably includes:

- admixing compound (V) with an organic solvent;
- optionally cooling to reduced temperature and adding a base;
- adding methanesulfonyl chloride, optionally in several portions, and reacting for sufficient time period to allow completing the reaction;
- filtering the thus formed suspension and obtaining a filtrate containing the crude product; and
- optionally using the filtrate in the next reaction.

The organic solvent used in the reaction can be toluene, xylenes, tetrahydrofuran (THF), 2-methyltetrahydrofuran, acetonitrile, and mixtures thereof. In some cases the organic solvent comprises THF.

The base used in the reaction is typically an organic amine. Amines contemplated for use in the process include, but are not limited to, triethylamine, tripropylamine, triisopropylamine, tributylamine, triisobutylamine, N,N-diisopropylethylamine (DIEA), N,N-dimethylaniline, or combinations thereof. In a specific embodiment, the base comprises N,N-diisopropylethylamine.

Reacting compound (III) with 1-(mercaptomethyl)cyclopropaneacetic acid (IV) in a solvent mixture and in the presence of a base preferably includes:

- admixing 1-(mercaptomethyl)cyclopropaneacetic acid (IV) with an organic solvent under stirring;
- admixing a base and optionally a co-solvent to afford a suspension;
- admixing the solution of compound (III) in an organic solvent, thus the solvent mixture containing a base is formed;

stirring for sufficient time period to allow completing the reaction; and optionally isolating montelukat acid as an oil.

The organic solvent is typically a polar solvent. Organic solvents contemplated for use in the process include, but are not limited to, N,N-dimethylformamide (DMF), N,N-dimethylacetamide (DMA), dimethyl sulfoxide (DMSO), N-methyl-pyrrolidone (NMP), tetrahydrofuran (THF), 2-methyltetrahydrofuran, acetonitrile, acetone, or mixtures thereof.

The organic solvent can be mixed with a co-solvent, such as water. The amount of the co-solvent is at least 1% by volume, and can be about 3% to about 10%, or about 4% to about 6% by volume, relative to the volume of the organic solvent.

Not bound by theory, it is postulated that a polar solvent, e.g., NMP with optional addition of about 5% water, efficiently dissolves the dianion of compound (IV) (e.g., a disodium dianion) and allows for better reaction between compound (IV) and compound (III).

The base is typically an inorganic base selected from alkaline and alkaline earth hydroxides, $C_1$-$C_4$ alkoxides and hydrides. Specific bases contemplated for use include, but are not limited to, sodium hydroxide, potassium hydroxide, lithium hydroxide, sodium hydride, sodium methoxide, and potassium methoxide. In a specific embodiment the base is sodium hydroxide, e.g., solid NaOH or NaOH solution.

The methansulfonyl chloride can be added to the cooled mixture of base and compound (V). The addition can be drop-wise or at least two portions. The methanesulfonyl chloride can be added in three portions, four portions, five portions, or six portions.

Montelukast acid can be isolated from the reaction of compound (IV) and compound (III) by adding an acid to the mixture. The acid can be either an inorganic acid or an organic acid. Specific organic acids contemplated for use include, but are not limited to, acetic acid, propionic acid, oxalic acid, benzoic acid, maleic acid, malonic acid, fumaric acid, tartaric acid, malic acid, citric acid, and combinations thereof. In a specific embodiment the organic acid comprises tartaric acid.

A process for preparing an ammonium salt of montelukast is disclosed herein. The process comprises admixing an amine and the reaction product of compound (IV) and compound (III) to obtain an ammonium salt of montelukast, and optionally purifying the ammonium salt of montelukast. Non-limiting examples of an amine include cyclohexylamine, cyclopentylamine, cycloheptylamine, cyclooctylamine, cyclododecylamine, and phenethylamine.

An organic solvent can be added to the reaction mixture prior to purifying the ammonium salt of montelukast. The organic solvent can be methyl acetate, ethyl acetate, n-propyl acetate, isopropyl acetate, n-butyl acetate, isobutyl acetate, chloroform, dichloromethane, toluene or mixtures thereof. Preferably, the organic solvent comprises toluene or ethyl acetate.

Purifying can be any means to remove impurities from the ammonium salt of montelukast, including, but not limited to, crystallizing the ammonium salt of montelukast, using chromatography or other separation techniques, extracting the ammonium salt of montelukast from impurities, filtering the ammonium salt of montelukast, or combinations of any two or more of these techniques. When crystallizing is used, the reaction mixture can optionally be seeded with a crystal of the ammonium salt of montelukast.

Crystallizing the ammonium salt of montelukast typically comprises adding an organic solvent to the ammonium salt of montelukast in order to promote crystallization. Typical organic solvents used include, but are not limited to, methanol, methyl acetate, ethyl acetate, n-propyl acetate, isopropyl acetate, n-butyl acetate, isobutyl acetate, toluene, and mixtures thereof. In some cases, the organic solvent comprises toluene or toluene having up to 5% methanol.

Further disclosed herein is a process for producing the sodium salt of montelukast from an ammonium salt, the process comprising:

admixing the ammonium salt, an acid, an organic solvent, and water;

separating the water; adding a base and water;

distilling off at least part of the organic solvent and obtaining an aqueous mixture of the final product; and drying the resulting aqueous mixture to obtain montelukast sodium.

According to one aspect of the present invention, the drying can be via spray-drying. The organic acid used can be any organic acid compatible with the process, but is typically acetic acid, propionic acid, oxalic acid, benzoic acid, maleic acid, malonic acid, fumaric acid, tartaric acid, malic acid, citric acid, or combinations thereof. In a specific embodiment, the organic acid is citric acid. Non-limiting examples of the organic solvent include methyl acetate, ethyl acetate, n-propyl acetate, isopropyl acetate, n-butyl acetate, isobutyl acetate, chloroform, dichloromethane, toluene and mixtures thereof. Preferably, the organic solvent comprises dichloromethane.

The process disclosed herein enables obtaining Compound (I) in a total yield of about 70%. The purity is at least 98.5%, and can be more than 99%, or greater than 99.5% (as determined by HPLC).

Reference is now made to the following examples, which together with the above descriptions, illustrate the invention in a non-limiting fashion. Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Example 1

Preparation of 2-(2-(3S)-(3-(7-chloro-2-quinolinyl) ethenyl)phenyl)-3-(methanesulfonyloxypropyl)phenyl-2-propanol (III)

A 500 ml 3-necked flask equipped with a thermometer, a nitrogen inlet and a magnetic stirrer was charged at room temperature with 3 g (0.0065 moles) of 2-(2-(3(S)-(3-(7-chloro-2-quinolinyl)ethenyl)phenyl)-3-(hydroxylpropyl) phenyl)-2-propanol (V) in 16 ml of anhydrous THF under stirring and cooled to about −15° C. 2.6 ml of N,N-diisopropylethylamine (DIEA) was added in portions followed by addition of 1.0 ml (0.013 moles) of methanesulfonyl chloride in portions, and stirring was maintained at about −15° C. for about 2 hours. A sample was withdrawn and checked by HPLC to ensure that no more than 1% of the starting material was present in the reaction mixture. The cold suspension containing the product 2-(2-(3S)-(3-(7-chloro-2-quinolinyl) ethenyl)phenyl)-3-(methanesulfonyloxypropyl)phenyl-2-propanol (III), was filtered at −15° C. and the cake was washed with cold anhydrous THF. The combined filtrate containing the product was used in the next step (example 2).

Example 2

Preparation of Montelukast Acid Cyclohexyl Ammonium Salt in a Solvent Mixture of DMF and THF Containing NaOH 47%

A 500 ml 3-necked flask equipped with a thermometer, a nitrogen inlet and a magnetic stirrer was charged at room temperature with 1.8 g (0.0123 moles) of 1-(mercaptomethyl) cyclopropaneacetic acid and 16 ml of DMF under stirring and under nitrogen atmosphere to obtain a solution. 1.8 ml of NaOH 47% (0.032 moles) was added drop-wise and stirring was maintained for 10 minutes to afford a suspension. The solution of compound (III) in 20 ml THF (from example 1) was added in portions at 25° C. After completing the addition, the mixture was stirred for 2 hours at 25° C. and reaction completion was checked by HPLC. 43 ml of ethyl acetate was added to the reaction mixture along with 43 ml of 5% sodium chloride solution. The mixture was stirred at 25° C. for 15 minutes. Then, the layers were separated and 28 ml of 0.5M tartaric acid was added to the upper layer and stirring was maintained at 25° C. for 15 minutes. The layers were separated and the upper layer was washed with 14 ml of water and again separated. The organic layer was distilled to dryness to afford an oily residue.

34 ml of ethyl acetate was added to the residue under stirring to obtain a solution. 0.8 ml of cyclohexylamine was added and stirring was maintained for few minutes at 25° C. and the solution was seeded with crystalline montelukast acid cyclohexyl ammonium salt. Stirring was maintained at 25° C. to afford a suspension, which was filtered off to obtain a cake. The cake was washed with ethyl acetate and dried at 40° C. in vacuum to afford 2.9 g of dry crude montelukast acid cyclohexyl ammonium salt in 65% Yield. The HPLC purity was 99%.

Example 3

Preparation of Montelukast Acid Cyclohexyl Ammonium Salt in a Solvent Mixture of DMF and THF Containing Solid NaOH

A 500 ml 3-necked flask equipped with a thermometer, a nitrogen inlet and a magnetic stirrer was charged at room temperature with 1.8 g (0.0123 moles) of 1-(mercaptomethyl) cyclopropaneacetic acid and 16 ml of DMF under stirring and under nitrogen atmosphere to obtain a solution. 1.4 g of NaOH pellets (0.035 moles) was added in portions and stirring was maintained for 1 hour to afford a suspension. Then, the solution of compound (III) in 20 ml THF (from example 1) was added in portions at 25° C. After completing the addition, the mixture was stirred for 5 hours at 25° C. and reaction completion was checked by HPLC. 43 ml of ethyl acetate was added to the reaction mixture along with 43 ml of 5% sodium chloride solution. The mixture was stirred at 25° C. for 20 minutes. Then, the layers were separated and 28 ml of 0.5 M tartaric acid was added to the upper layer and stirring was maintained at 25° C. for 15 minutes. The layers were separated and the upper layer was washed with 14 ml of water and again separated. The organic layer was distilled to dryness to afford an oily residue.

34 ml of ethyl acetate was added to the residue under stirring to obtain a solution. 0.8 ml of cyclohexylamine was added and stirring was maintained for few minutes at 25° C. and the solution was seeded with crystalline montelukast acid cyclohexyl ammonium salt. Stirring was maintained at 25° C. to afford a suspension, which was filtered off to obtain a cake. The cake was washed with ethyl acetate and dried at 40° C. in vacuum to afford 3.1 g of dry crude montelukast acid cyclohexyl ammonium salt in 70% Yield. The HPLC purity was 99%.

Example 4

Preparation of Montelukast Acid Cycloheptyl Ammonium Salt in a Solvent Mixture of DMF and THF Containing NaOH 47%

A 500 ml 3-necked flask equipped with a thermometer, a nitrogen inlet and a magnetic stirrer was charged at room temperature with 1.8 g (0.0123 moles) of 1-(mercaptomethyl) cyclopropaneacetic acid and 16 ml of DMF under stirring and under nitrogen atmosphere to obtain a solution. 2.0 ml of NaOH 47% (0.035 moles) was added drop-wise and stirring was maintained for 10 minutes to afford a suspension. A solution of 3 g of compound (III) in 20 ml THF was added in portions at 25° C. After completing the addition, the mixture was stirred for 2 hours at 25° C. and reaction completion was checked by HPLC. 43 ml of ethyl acetate was added to the reaction mixture and 43 ml of 5%. sodium chloride solution. The mixture was stirred at 25° C. for 15 minutes.

Then, the layers were separated and 28 ml of 0.5 M tartaric acid was added to the upper layer and stirring was maintained at 25° C. for 15 minutes. The layers were separated and the upper layer was washed with 14 ml of water and again separated. The organic layer was distilled to dryness to afford an oily residue.

34 ml of ethyl acetate was added to the residue under stirring to obtain a solution. 0.89 ml of cycloheptylamine was added and stirring was maintained for few minutes at 25° C. and the solution was seeded with crystalline montelukast acid cycloheptyl ammonium salt. Stirring was maintained at 25° C. to afford a suspension, which was filtered to obtain a cake. The cake was washed with ethyl acetate and dried at 40° C. in vacuum to afford 2.7 g of dry crude montelukast acid cycloheptyl ammonium salt in 65% yield, having a purity of 98% (according to HPLC).

Example 5

Preparation of Montelukast Sodium

A three-necked flask equipped with a thermometer, a nitrogen inlet and a magnetic stirrer was charged at room temperature with 9.06 g (0.0198 moles) of 2-(2-(3(S)-(3-(7-chloro-2-quinolinyl)ethenyl)phenyl)-3-(hydroxylpropyl)phenyl)-2-propanol (V) in 48 ml of anhydrous THF under stirring and cooled to about −20° C. 4.8 ml (0.028 moles) of N,N-diisopropylethylamine (DIEA) was added in portions followed by addition of 1.86 ml (0.024 moles) of methanesulfonyl chloride in portions, and stirring was maintained at about −20° C. for about 2 hours. The cold suspension containing the product 2-(2-(3S)-(3-(7-chloro-2-quinolinyl)ethenyl)phenyl)-3-(methanesulfonyloxypropyl)phenyl-2-propanol (III), was filtered off at −20° C. and the cake was washed with cold anhydrous THF. The combined solutions of compound (III) in THF was kept aside at 5° C.

Another three-necked flask equipped with a thermometer, a nitrogen inlet and a magnetic stirrer was charged at room temperature with 6.7 g (0.0459 moles) of 1-(mercaptomethyl) cyclopropaneacetic acid and 48 ml of NMP under stirring and under nitrogen atmosphere to obtain a solution. 4.5 g of NaOH flakes (0.1125 moles) was added in one portion at room temperature followed by addition of 2.4 ml of water, and stirring was maintained for 1 hour to afford a suspension. The solution of compound (III) in about 50 ml THF, which was kept at 5° C., was added in portions at ambient temperature. After completing the addition, the mixture was stirred for 2 hours and reaction completion was checked by HPLC. 130 ml of toluene was added to the reaction mixture along with 130 ml of 5% sodium chloride solution, and the mixture was stirred for 20 minutes. Then, the layers were separated and the upper organic layer was washed with 130 ml of 5% sodium chloride solution, and the layers were separated. 84 ml of 0.5 M tartaric acid solution was added to the upper layer and the layers were separated. The upper layer was washed with 40 ml of water and again separated. The organic layer was distilled to dryness to afford an oily residue. 90 ml of toluene was added to the residue under stirring to obtain a solution. 3.1 ml of cyclooctylamine (0.0226 moles) was added and stirring was maintained for few minutes and the solution was seeded with crystalline montelukast acid cyclooctyl ammonium salt. Stirring was maintained at room temperature to afford a suspension, which was filtered off to obtain a cake. The cake was washed with toluene and dried at 40° C. in vacuum to afford 9.88 g of dry crude montelukast acid cyclooctyl ammonium salt in 70% yield, having 98% purity (according to HPLC). The crude montelukast cyclooctyl ammonium salt was crystallized from toluene containing about 2% of methanol to obtain a product having 99% purity (according to HPLC). 30 ml of dichloromethane was added followed by addition of 17 ml of 0.5M citric acid solution. The mixture was stirred at room temperature for half an hour to afford a two phase system. The layers were separated and the organic layer (containing the montelukast acid) was washed with 3×15 ml water, the layers were separated and the aqueous layer was removed. 20 ml of water was added under stirring followed by addition of 4 ml of 1M NaOH solution and stirring was maintained for about 5 minutes. The dichloromethane was distilled off at a temperature lower than 35° C. The pH was checked and 1 M NaOH solution was added drop-wise until the pH value was about 10.5. The aqueous layer (containing the desired end product) was freeze-dried to obtain 8.3 g of montelukast sodium in 99% yield having a purity of 99.8% (according to HPLC).

What is claimed is:

1. A process for preparing montelukast sodium having a purity of at least 99%, the process comprising:
    reacting 2-(2-(3(S)-(3-(7-chloro-2-quinolinyl)ethenyl) phenyl)-3-(hydroxyl-propyl)phenyl)-2 propanol (compound V) with methanesulfonyl chloride, to thereby obtain 2-(2-(3S)-(3-(7-chloro-2-quinolinyl)ethenyl) phenyl)-3-(methanesulfonyloxypropyl)-phenyl-2-propanol (compound III);
    reacting compound (III) with 1-(mercaptomethyl)cyclopropaneacetic acid (compound IV) in the presence of a base selected from the group consisting of sodium hydroxide, potassium hydroxide, lithium hydroxide, sodium hydride, sodium methoxide, and potassium methoxide, to thereby obtain montelukast acid;
    adding an organic amine selected from the group consisting of cyclohexylamine, cyclopentylamine, cycloheptylamine, cyclooctylamine, cyclododecylamine, and phenethylamine to said montelukast acid and isolating an addition ammonium salt of montelukast; and
    converting the addition ammonium salt of montelukast to montelukast sodium, thereby obtaining the montelukast sodium salt having a purity of at least 99% (as determined by HPLC).

2. The process of claim 1, wherein reacting said compound (V) with said methanesulfonyl chloride comprises:
    admixing compound (V) with an organic solvent;
    adding a base selected from the group consisting of triethylamine, tripropylamine, triisopropylamine, tributylamine, triisobutylamine, N,N-diisopropylethylamine (DIEA), and N,N-dimethylaniline;
    adding said methanesulfonyl chloride, optionally in several portions, and mixing for sufficient time period to allow completing the reaction, to thereby obtain a suspension; and
    filtering said suspension to thereby obtain a filtrate containing said compound (III) in said organic solvent.

3. The process of claim 2, wherein said organic solvent is selected from the group consisting of toluene, xylenes, tetrahydrofuran (THF), 2-methyltetrahydrofuran, acetonitrile, and mixtures thereof.

4. The process of claim 2, wherein said organic solvent is tetrahydrofluran (THF).

5. The process of claim 2, wherein said base is diisopropylethylamine (DIEA).

6. The process of claim 1, wherein reacting compound (III) with 1-(mercaptomethyl)-cyclopropaneacetic acid (compound IV) comprises:
    admixing 1-(mercaptomethyl)cyclopropaneacetic acid (compound IV) with an organic solvent under stirring;
    admixing said 1-(mercaptomethyl)cyclopropaneacetic acid (compound IV) and said organic solvent with said base and optionally with a co-solvent, to thereby afford a suspension;
    admixing said suspension with a solution of compound (III) in an organic solvent;
    stirring for sufficient time period to allow reaction completion; and
    optionally isolating montelukat acid as an oil.

7. The process of claim 6, wherein said organic solvent is selected from the group consisting of N,N-dimethylformamide (DMF), N,N-dimethylacetamide (DMA), dimethyl sulfoxide (DMSO), N-methyl-pyrrolidone (NMP), tetrahydrofuran (THF), 2-methyltetrahydrofuran, acetonitrile, acetone, and mixtures thereof.

8. The process of claim 6, wherein said organic solvent is N-methyl-pyrrolidone (NMP) and said co-solvent is water.

9. The process of claim 6, wherein an amount of said co-solvent is at least 1% by volume of the volume of said organic solvent.

10. The process of claim 9, wherein said amount of said co-solvent is about 3% to about 10% by volume of the volume of said organic solvent.

11. The process of claim 10, wherein said amount of said co-solvent is about 4% to about 6% by volume of the volume of said organic solvent.

12. The process of claim 1, wherein said base is sodium hydroxide.

13. The process of claim 6, wherein isolating said montelukast acid is carried out by adding an aqueous solution of an acid to the mixture.

14. The process of claim 13, wherein said acid is selected from the group consisting of acetic acid, propionic acid, oxalic acid, benzoic acid, maleic acid, malonic acid, fumaric acid, tartaric acid, malic acid, citric acid, and combinations thereof.

15. The process of claim 14, wherein said acid is tartaric acid.

16. The process of claim 1, wherein isolating said montelukast addition ammonium salt comprises:

admixing said organic amine and said montelukast acid obtained by reacting compound (IV) and compound (III), to thereby obtain an ammonium salt of montelukas; and purifying said ammonium salt of montelukast.

17. The process of claim 1, wherein said organic amine is cyclooctylamine.

18. The process of claim 16, wherein purifying said ammonium salt of montelukast is carried out by adding an organic solvent to a mixture containing said organic amine and said montelukast acid, said organic solvent being selected from the group consisting of methyl acetate, ethyl acetate, n-propyl acetate, isopropyl acetate, n-butyl acetate, isobutyl acetate, chloroform, dichloromethane, toluene, and mixtures thereof.

19. The process of claim 18, wherein said organic solvent is toluene or ethyl acetate.

20. The process of claim 16, wherein said purifying comprises removing impurities from said ammonium salt of montelukast, by a method selected from crystallization of said ammonium salt of montelukast, chromatography extraction of said ammonium salt of montelukast filtration of said ammonium salt of montelukast, or combinations of any two or more of these techniques.

21. The process of claim 20, wherein an organic solvent used for said crystallization is selected from the group consisting of methanol, methyl acetate, ethyl acetate, n-propyl acetate, isopropyl acetate, n-butyl acetate, isobutyl acetate, toluene, and mixtures thereof.

22. The process of claim 21, wherein said organic solvent used for said crystallization is toluene having up to 5% methanol.

23. The process of claim 1, wherein converting said addition ammonium salt of montelukast to montelukast sodium comprises:

admixing said ammonium salt of montelykast, an acid, an organic solvent, and water;

separating an aqueous phase containing said water;

adding a base and water;

distilling off at least part of the organic solvent, to thereby obtain an aqueous mixture containing the montelukast sodium; and drying said aqueous mixture, to thereby obtain montelukast sodium.

24. The process of claim 23, wherein said drying is effected by spray-drying.

25. The process of claim 23, wherein said organic acid is selected from the group consisting of acetic acid, propionic acid, oxalic acid, benzoic acid, maleic acid, malonic acid, fumaric acid, tartaric acid, malic acid, citric acid, and combinations thereof.

26. The process of claim 25, wherein said organic acid is citric acid.

27. The process of claim 23, wherein said organic solvent is selected from the group consisting of methyl acetate, ethyl acetate, n-propyl acetate, isopropyl acetate, n-butyl acetate, isobutyl acetate, chloroform, dichloromethane, toluene and mixtures thereof.

28. The process of claim 27, wherein said organic solvent is dichloromethane.

29. The process of claim 1, wherein said purity is greater than 99.5% (as determined by HPLC).

* * * * *